United States Patent
Belanoff et al.

(10) Patent No.: US 11,173,165 B2
(45) Date of Patent: *Nov. 16, 2021

(54) OPTIMIZING MIFEPRISTONE LEVELS FOR CUSHING'S PATIENTS

(71) Applicant: Corcept Therapeutics, Inc., Menlo Park, CA (US)

(72) Inventors: Joseph Belanoff, Woodside, CA (US); Coleman Gross, Menlo Park, CA (US)

(73) Assignee: Corcept Therapeutics, Inc., Menlo Park, CA (US)

( * ) Notice: Subject to any disclaimer, the term of this patent is extended or adjusted under 35 U.S.C. 154(b) by 85 days.

This patent is subject to a terminal disclaimer.

(21) Appl. No.: 16/866,887

(22) Filed: May 5, 2020

(65) Prior Publication Data

US 2020/0261471 A1    Aug. 20, 2020

Related U.S. Application Data

(63) Continuation of application No. 16/219,496, filed on Dec. 13, 2018, now Pat. No. 10,660,904, which is a continuation of application No. 16/146,032, filed on Sep. 28, 2018, now Pat. No. 10,166,243, which is a continuation of application No. 15/919,719, filed on Mar. 13, 2018, now Pat. No. 10,166,242, which is a continuation of application No. 15/133,791, filed on Apr. 20, 2016, now Pat. No. 9,943,526.

(60) Provisional application No. 62/150,757, filed on Apr. 21, 2015.

(51) Int. Cl.
| | |
|---|---|
| A61K 31/567 | (2006.01) |
| A61K 31/136 | (2006.01) |
| A61K 31/122 | (2006.01) |
| A61K 31/135 | (2006.01) |
| G01N 33/94 | (2006.01) |

(52) U.S. Cl.
CPC .......... *A61K 31/567* (2013.01); *A61K 31/122* (2013.01); *A61K 31/135* (2013.01); *A61K 31/136* (2013.01); *G01N 33/94* (2013.01); *G01N 2800/048* (2013.01); *G01N 2800/52* (2013.01)

(58) Field of Classification Search
CPC ... A61K 31/567; A61K 31/122; A61K 31/135
See application file for complete search history.

(56) References Cited

U.S. PATENT DOCUMENTS

| | | | |
|---|---|---|---|
| 6,150,349 A | 11/2000 | Schatzberg et al. | |
| 6,369,046 B1 | 4/2002 | Schatzberg et al. | |
| 6,620,802 B1 | 9/2003 | Schatzberg et al. | |
| 6,680,310 B2 | 1/2004 | Belanoff et al. | |
| 6,964,953 B2 | 11/2005 | Belanoff | |
| 7,163,934 B2 | 1/2007 | Belanoff | |
| 7,326,697 B2 | 2/2008 | Schatzberg et al. | |
| 7,361,646 B2 | 4/2008 | Belanoff | |
| 7,402,578 B2 | 7/2008 | Belanoff | |
| 8,097,606 B2 | 1/2012 | Belanoff | |
| 8,598,149 B2 | 12/2013 | Belanoff | |
| 8,921,348 B2 | 12/2014 | Belanoff | |
| 9,943,526 B2 | 4/2018 | Belanoff et al. | |
| 10,166,242 B2 | 1/2019 | Belanoff et al. | |
| 10,166,243 B1 | 1/2019 | Belanoff et al. | |
| 10,500,216 B2 | 12/2019 | Belanoff et al. | |
| 10,660,904 B2 | 5/2020 | Belanoff et al. | |
| 2004/0132703 A1 | 7/2004 | Belanoff | |
| 2004/0229855 A1 | 11/2004 | Belanoff | |
| 2006/0063748 A1 | 3/2006 | Belanoff | |
| 2007/0238779 A1 | 10/2007 | Roberts et al. | |
| 2007/0254025 A1 | 11/2007 | Cronk | |
| 2010/0179115 A1 | 7/2010 | Belanoff | |
| 2010/0261693 A1 | 10/2010 | Ulmann et al. | |
| 2011/0144072 A1 | 6/2011 | Belanoff | |
| 2011/0166115 A1 | 7/2011 | Belanoff | |
| 2011/0294771 A1 | 12/2011 | Belanoff | |
| 2013/0131030 A1 | 5/2013 | Belanoff et al. | |
| 2014/0162993 A1 | 6/2014 | Belanoff | |
| 2016/0310507 A1 | 10/2016 | Belanoff et al. | |

FOREIGN PATENT DOCUMENTS

WO    2009050136    4/2009

OTHER PUBLICATIONS

U.S. Appl. No. 16/219,496, filed Dec. 13, 2018.
U.S. Appl. No. 16/146,032, filed Sep. 28, 2018.
U.S. Appl. No. 15/919,719, filed Mar. 13, 2018.
U.S. Appl. No. 15/133,791, filed Apr. 20, 2016.
"Food-Effect Bioavailability and Fed Bioequivalence Studies", Guidance for Industry: U.S. Department of Health and Human Services, Food and Drug Administration, Center for Drug Evaluation and Research (CDER), Dec. 2002, 12 pages.
"Medical Encyclopedia: Therapeutic Drug Levels", MedlinePlus, Available Online at: http://www.nlm.nih.gov/medlineplus/ency/articie/003430.htm, Oct. 2005, 4 pages.
"The Biopharmaceutics Classification System (BCS) Guidance", Available on Internet at: https://www.fda.gov/AboutFDA/CentersOffices/OfficeofMedicaiProductsandTobacco/CDER/ucm128219.htm, Accessed from internet on Oct. 17, 2017, 4 pages.

(Continued)

Primary Examiner — Yong S. Chong

(74) Attorney, Agent, or Firm — Kilpatrick Townsend & Stockton LLP

(57) ABSTRACT

The present invention provides a method for optimizing levels of mifepristone in a patient suffering from Cushing's syndrome. The method comprises the steps of treating the patient with seven or more daily doses of mifepristone over a period of seven or more days; testing the serum levels of the patient to determine whether the blood levels of mifepristone are greater than 1631 ng/mL; and adjusting the daily dose of the patient to achieve mifepristone blood levels greater than 1631 ng/mL.

15 Claims, No Drawings

(56) References Cited

OTHER PUBLICATIONS

"The New Drug Application (NDA) BA and BE Draft Guidance (Guidance for Industry. Bioavailability and Bioequivalence Studies Submitted in NDAs or INDs—General Considerations", U.S. Department of Health and Human Services, Food and Drug Administration, Center for Drug Evaluation and Research, Biopharmaceutics, https://www.fda.gov/downloads/drugs/guidancecomplianceregulatotyinformation/guidances/ucm389370.pdf, Mar. 2014, 29 pages.

Aanderud et al., "Plasma Cortisol Concentrations after Oral Substitution of Cortisone in the Fasting and Non-Fasting State", Acta Medica Scandinavica, vol. 210, Issue 1-6, 1981, pp. 157-161.

Bagchus et al., "Important Effect of Food on the Bioavailability of Oral Testosterone Undecanoate", Pharmacotherapy, vol. 23, No. 3, Mar. 2003, pp. 319-325.

Belanoff et al., "An Open Label Trial of C-1073 (Mifepristone) for Psychotic Major Depression", Biological Psychiatry, vol. 52, Issue 1, Sep. 2002, pp. 386-392.

Berthois et al., "A Multiparametric Analysis of Endometrial Estrogen and Progesterone Receptors After the Postovulatory Administration of Mifepristone", Fertility and Sterility, vol. 55, Issue 3, Mar. 1991, pp. 547-554.

Cassier et al., "Mifepristone for Ectopic ACTH Secretion in Metastic Endocrine Carcinomas: Report of Two Cases", European Journal of Endocrinology, vol. 158, No. 6, Jun. 2008, pp. 935-938.

Castinetti et al., "Medical Treatment of Cushing's Syndrome: Glucocorticoid Receptor Antagonists and Mifepristone", Neuroendocrinology, vol. 92, 2010, pp. 125-130.

Castinetti et al., "Merits and Pitfalls of Mifepristone in Cushing's Syndrome", European Journal of Endocrinology, vol. 160, No. 6, 2009, pp. 1003-1010.

Chu et al., "Successful Long-Term Treatment of Refractory Cushing's Disease with High-Dose Mifepristone (RU 486)", The Journal of Clinical Endocrinology & Metabolism, vol. 86, No. 8, Aug. 1, 2001, pp. 3568-3573.

Davis et al., "Guidelines for Counselling Patients Receiving Drugs Used in the Treatment of Neoplastic Disease: A Pharmacist's Guide to Advisory Labels and Patient Information", The Australian Journal of Hospital Pharmacy, vol. 31, No. 1, Mar. 2001, pp. 51-55.

Fleseriu et al., "Mifepristone, a Glucocorticoid Receptor Antagonist, Produces Clinical and Metabolic Benefits in Patients with Cushing's Syndrome", The Journal of Clinical Endocrinology & Metabolism, vol. 97, No. 6, Jun. 2012, pp. 2039-2049.

Gross et al., "Mifepristone Reduces Weight Gain and Improves Metabolic Abnormalities Associated With Risperidone Treatment in Normal Men", Obesity, vol. 18, Issue No. 12, Dec. 2010.

Heikinheimo et al., "Clinical Pharmacokinetics of Mifepristone", Clinical Pharmacokinetics, vol. 33, No. 1, Jul. 1997, pp. 7-17.

Heikinheimo et al., "The Pharmacokinetics Ofmifepristone in Humans Reveal Insights Into Differential Mechanisms of Anti Progestin Action", Contraception, vol. 68, 2003, pp. 421-426.

Hofsaess et al., "Establishing the BCS Classification of APis Recently Added to the WHO Essential Medicines List", Poster Presentation at the 2015 AAPS Annual Meeting and Exposition, St. Louis, MO, Poster T2064, 2015, 1 page.

Johanssen et al., "Mifepristone (RU 486) in Cushing's Syndrome", European Journal of Endocrinology, vol. 157, No. 5, 2007, pp. 561-569.

Kawai et al., "Pharmacokinetic Properties of the Antiglucocorticoid and Antiprogesterone Steroid RU 486 in Man", The Journal of Pharmacology and Experimental Therapeutics, vol. 241, No. 2, May 1987, pp. 401-406.

Lee et al., "Office of Clinical Pharmacology Review", NDA 20687 (Addendum, Korlym ™, Mifepristone), 2012, pp. 1-119.

Lignieres , "Oral Micronized Progesterone", Clinical Therapeutics, vol. 21, Issue 1, Jan. 1999, pp. 41-60.

Lindberg , "Emergency Contraception: The Nurse's Role in Providing Postcoital Options", Journal of Obstetric, Gynecologic, & Neonatal Nursing, vol. 26, No. 2, Mar.-Apr. 1997, pp. 146-152.

Luft , "Novel Cell Therapy for Type 1 Diabetes Mellitus", Journal of Molecular Medicine, vol. 87, 2009, pp. 659-661.

Nieman et al., "Successful Treatment of Cushing's Syndrome with the Glucocorticoid Antagonist RU 486", Journal of Clinical Endocrinology Metabolism, vol. 61, No. 3, Sep. 1, 1985, pp. 536-540.

Para et al., "Phase I/II Trial of the Anti-Hiv Activity of Mifepristone in Hiv-lnfected Subjects ACTG 5200", Journal of Acquired Immune Deficiency Syndromes,vol. 53, No. 4, Apr. 1, 2010, pp. 491-495.

Saav et al., "Medical Abortion in Lactating Women—Low Levels of Mifepristone in Breast Milk", Acta Obstetricia Et Gynecologica Scandinavica, vol. 89, No. 5 •, Mar. 2010, pp. 618-622.

Sarkar , "Mifepristone: Bioavailability, Pharmacokinetics and Use-effectiveness", European Journal of Obstetrics and Gynecology and Reproductive Biology, vol. 101, Issue No. 2, Mar. 10, 2002, pp. 113-120.

Sartor et al., "Mifepristone: Treatment of Cushing's Syndrome", Clinical Obstetrics Gynecol, vol. 39, No. 2, Jun. 1996, pp. 506-510.

Sitruk-Ware et al., "Pharmacological Properties of Mifepristone: Toxicology and Safety in Animal and Human Studies", Contraception, vol. 68, 2003, pp. 409-420.

Tsigos , "Differential Diagonsis and Management of Cushing's Syndrome", Annu. Rev. Med., vol. 47, 1996, pp. 443-461.

Welling , "Effects of Food on Drug Absorption", Annu. Rev. Nutr., vol. 16, 1996, pp. 383-415.

Winstanley et al., "The Effects of Food on Drug Bioavailability", British Journal of Clinical Pharmacology, vol. 28, Dec. 1989, pp. 621-628.

OPTIMIZING MIFEPRISTONE LEVELS FOR CUSHING'S PATIENTS

CROSS-REFERENCES TO RELATED APPLICATIONS

This application is a Continuation of U.S. patent application Ser. No. 16/219,496, filed Dec. 13, 2018, which is a Continuation of U.S. patent application Ser. No. 16/146,032, filed Sep. 28, 2018 (now U.S. Pat. No. 10,166,243, issued Jan. 1, 2019), which is a Continuation of U.S. patent application Ser. No. 15/919,719, filed Mar. 13, 2018 (now U.S. Pat. No. 10,166,242, issued Jan. 1, 2019), which is a Continuation of U.S. patent application Ser. No. 15/133,791, filed Apr. 20, 2016 (now U.S. Pat. No. 9,943,526, issued Apr. 17, 2018), which claims priority to and the benefit of U.S. Provisional Application No. 62/150,757, filed Apr. 21, 2015, the applications of which are incorporated in their entireties herein for all purposes.

BACKGROUND OF THE INVENTION

It has been reported previously that administration of the same dose of mifepristone can produce widely varying blood serum levels in different patients. The varied blood serum levels can result in some patients not receiving an efficacious dose of mifepristone. For patients suffering from a mental disorder, the blood serum levels need to be maintained at about 1300 ng/mL. For patients suffering from Cushing's syndrome, it was surprisingly discovered that blood serum levels need to be maintained at a level of at least about 1631 ng/mL for a therapeutic response. Thus, a method for ensuring that the blood serum levels of mifepristone remain in an efficacious and safe range is needed for patients suffering from Cushing's syndrome.

BRIEF SUMMARY OF THE INVENTION

In one embodiment, the present invention provides a method for improving efficacy of mifepristone treatment in a patient suffering from Cushing's syndrome. The method includes treating the patient with seven or more daily doses of mifepristone over a period of seven or more days; testing the serum levels of the patient to determine whether the blood levels of mifepristone are greater than 1631 ng/mL; and adjusting the daily dose of the patient to achieve mifepristone blood levels greater than 1631 ng/mL. The patient of the present invention is not already suffering from a condition indicated for treatment with mifepristone. Thus, the method thereby improves the efficacy of mifepristone treatment for patients suffering from Cushing's syndrome for the patient suffering from Cushing's syndrome.

DETAILED DESCRIPTION OF THE INVENTION

I. Introduction

Administration of the same dose of mifepristone can produce widely varying mifepristone blood serum levels in different patients. For the same dose, the blood serum levels can differ by as much as 800% from one patient to another. For those patients with lower blood serum levels, the effectiveness of mifepristone treatment can suffer significantly. The present invention provides a method for optimizing the blood serum levels of mifepristone so that the blood serum levels remain in an efficacious range and the patient receives the necessary treatment.

The method of the present invention optimizes blood serum levels of mifepristone in a patient suffering from Cushing's syndrome by first treating the patient with mifepristone. The treatment can be for any appropriate period of time, such as seven or more daily doses over a period of seven or more days. Following treatment for an appropriate period of time, the serum levels of the patient are tested to determine whether the blood levels of mifepristone are greater than 1631 ng/mL. The daily dose of the patient is then adjusted in order to achieve mifepristone blood levels of greater than 1631 ng/mL.

Previous methods of optimizing mifepristone levels are known for patients suffering from mental disorders. But the earlier methods describe a minimum mifepristone blood level of only 1300 ng/mL. While patients with Cushing's syndrome are known to have higher cortisol levels, it is surprising that higher mifepristone blood level of 1631 ng/mL would be necessary to achieve optimal efficacy in treating Cushing's syndrome.

II. Definitions

"Mifepristone" refers to a compound having the following structure:

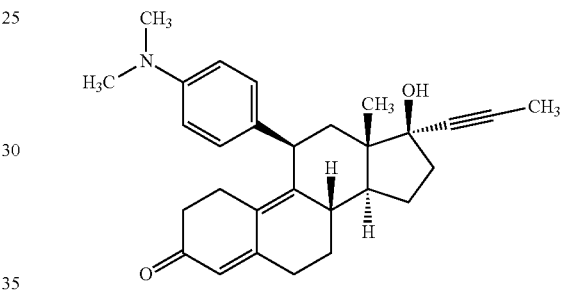

The term mifepristone also refers to a family of compositions also known as: RU486 or RU38.486; 17-beta-hydroxy-11-beta-(4-dimethyl-aminophenyl)-17-alpha-(1-propynyl)-estra-4,9-dien-3-one); 11-beta-(4dimethylaminophenyl)-17-beta-hydroxy-17-alpha-(1-propynyl)-estra-4,9-dien-3-one); 11B-[p-(Dimethylamino) phenyl]-17B-hydroxy-17-(1-propynyl)-estra-4,9-dien-3-one; 11B-(4-dimethyl-aminophenyl)-17B-hydroxy-17A-(prop-1-ynyl)-estra-4,9-dien-3-one; 17B-hydroxy-11B-(4-dimethylaminophenyl-1)-17A-(propynyl-1)-estra-4,9-diene-3-one; 17B-hydroxy-11B-(4-dimethylaminophenyl-1)-17A-(propynyl-1)-E; (11B,17B)-11-[4-dimethylamino)-phenyl]-17-hydroxy-17-(1-propynyl)estra-4,9-dien-3-one; and 11B-[4-(N,N-dimethylamino) phenyl]-17A-(prop-1-ynyl)-D-4,9-estradiene-17B-ol-3-one. Salts, hydrates and prodrug forms of mifepristone are also useful in the formulations of the present invention.

Mifepristone and its analogs bind to the glucocorticoid receptor (GR), typically with high affinity, and inhibit the biological effects initiated/mediated by the binding of any cortisol or cortisol analogue to the GR. As such, mifepristone has been used to treat conditions associated with elevated cortisol levels including, for example, hyperadrenocorticism, also known as Cushing's syndrome (Chrousos, pp 273-284, In: Baulieu, ed. *The Antiprogestin Steroid RU 486 and Human Fertility Control*. Plenum Press, New York (1989), Sartor (1996) *Clin. Obstetrics and Gynecol.* 39:506-510). Patients with some forms of psychiatric illnesses can be responsive to treatments which block the effect of cortisol, as by administering GR antagonists (Van Look (1995) *Human Reproduction Update* 1:19-34). In one study, a patient with depression associated with Cushing's Syndrome was responsive to a high dose, up to 1400 mg per day, of mifepristone (Nieman (1985) *J. Clin Endocrinol. Metab.* 61:536). Due to its antiprogestogenic activity, mifepristone has also been employed in emergency contraception, medical abortion, and treatment of uterine fibroids and meningioma (Healy (2009) *Australian Prescriber* 32:152-154).

"Patient" refers to animals such as mammals, including, but not limited to, primates (e.g., humans), cows, sheep, goats, horses, dogs, cats, rabbits, rats, mice and the like. The patient can have a condition known to be treated by glucocorticoid antagonists such as mifepristone. Such conditions include, but are not limited to, psychiatric illnesses and hormonal disorders. In certain embodiments, the patient is a human. The patient can be male or female.

"Cushing's syndrome" refers to an endocrine disease with an estimated incidence of approximately 10-15 per 1 million persons (Meier and Biller (1997) *Endocrinol Metab Clin North Am* 26:741-762), and is associated with an increased blood concentration of cortisol (hypercortisolism) over a long period of time. Cushing's syndrome is classified as either ACTH dependent or non ACTH dependent. ACTH dependent Cushing's syndrome is characterized by a chronic ACTH hypersecretion which stimulates the growth of the adrenal glands and the hypersecretion of corticosteroids. The most common underlying cause of ACTH dependent Cushing's syndrome is excessive production of ACTH by pituitary adenomas known as Cushing's disease. Cushing's syndrome resulting from the production of ACTH in another location than the pituitary gland is known as ectopic Cushing's syndrome. Examples of ectopic sites include thymoma, medullary carcinoma of the thyroid, pheochromocytoma, islet cell tumors of the pancreas and small cell carcinoma of the lung. ACTH independent Cushing's syndromes are caused by adrenal tumors that can be either adenomas or carcinomas. Both adrenal adenomas and carcinomas are characterized by chronic cortisol hypersecretion.

"Optimizing" refers to the process of testing mifepristone blood levels and adjusting the dosage of mifepristone administered to the patient in need in order to achieve mifepristone blood levels above 1631 ng/mL.

"Treat", "treating" and "treatment" collectively refer to any indicia of success in the treatment or amelioration of an injury, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being; or, in some situations, preventing the onset of dementia. The treatment or amelioration of symptoms can be based on objective or subjective parameters; including the results of a physical examination, neuropsychiatric exams, and/or a psychiatric evaluation.

"Testing" refers to determining the mifepristone blood levels in a patient. The testing can be performed by any suitable instrument, such as a plasma sampling collection device capable of detecting mifepristone serum levels.

A patient "not already suffering from a condition indicated for treatment with mifepristone" is a patient who is not suffering from a condition which is known in the art to be effectively treatable with mifepristone. Conditions known in the art to be effectively treatable with mifepristone include drug withdrawal, psychosis, dementia, stress disorders, and psychotic major depression.

III. Method of Optimizing Mifepristone Levels

The present invention provides a method of optimizing mifepristone levels in patients with Cushing's syndrome such that the blood serum levels remain at efficacious levels. The method involves administering mifepristone for a week, testing the blood serum levels of the Cushing's patient, and adjusting the mifepristone dose to maintain the mifepristone blood serum levels of at least 1631 ng/mL.

The present invention provides a method for improving efficacy of mifepristone treatment in a patient suffering from Cushing's syndrome. The method includes treating the patient with seven or more daily doses of mifepristone over a period of seven or more days; testing the serum levels of the patient to determine whether the blood levels of mifepristone are greater than 1631 ng/mL; and adjusting the daily dose of the patient to achieve mifepristone blood levels greater than 1631 ng/mL. The patient treated in this method is not already suffering from a condition indicated for treatment with mifepristone, thereby improving the efficacy of mifepristone treatment for the patient suffering from Cushing's syndrome.

The seven or more daily doses of mifepristone can each be administered by any means suitable, as described in more detail below. In some embodiments, each of the seven or more daily doses of mifepristone are administered orally.

The seven or more daily doses of mifepristone can each be administered in any suitable dose. For example, the mifepristone can be administered in an amount of at least about 100 mg. The mifepristone can also be administered in an amount of about 300, 600, 900 or about 1200 mg. In some embodiments, the daily dose can be at least 300 mg. In some embodiments, the daily dose can be at least 600 mg. In some embodiments, the daily dose can be at least 900 mg. In some embodiments, the daily dose can be at least 1200 mg. Other daily doses are useful in the method of the present invention.

The daily doses can be administered for any suitable period of time that is at least 7 days in length. For example, the daily doses can be for 7, 8, 9, 10, 11, 12, 13, 14, 15, 16, 17, 18, 19, 20, 21, 22, 23, 24, 25, 26, 27, or 28 days. The mifepristone can be administered for longer periods as required by the patient being treated. In some embodiments, the patient can be treated with 28 or more daily doses over a period of 28 or more days.

The mifepristone blood levels can be tested by any means known to one of skill in the art. For example, the testing can be performed by a plasma sampling collection device suitable for detecting mifepristone serum levels.

The mifepristone blood levels can be at any suitable level to treat Cushing's syndrome. For example, the mifepristone blood levels can be greater than about 1400 ng/mL, 1450, 1500, 1550, 1600, 1650, 1700, 1750, 1800, 1850, 1900, 2100, 2200, 2300, 2400, 2500, 2600, 2700, 2800 or great than about 2900 ng/mL. In some embodiments, the mifepristone blood level can be greater than 1450 ng/mL. In some embodiments, the mifepristone blood level can be greater than 1469 ng/mL. In some embodiments, the mifepristone blood level can be greater than 1600 ng/mL. In some embodiments, the mifepristone blood level can be greater than 1631 ng/mL. In some embodiments, the mifepristone blood level can be greater than 1662 ng/mL. In some embodiments, the mifepristone blood level can be greater than 1666 ng/mL. In some embodiments, the mifepristone blood level can be greater than 1700 ng/mL. In some embodiments, the mifepristone blood level can be greater than 1800 ng/mL. In some embodiments, the mifepristone blood level can be greater than 1820 ng/mL. In some embodiments, the mifepristone blood level can be greater than 2000 ng/mL. In some embodiments, the mifepristone blood level can be greater than 2022 ng/mL.

The daily dose can be adjusted to any suitable dose to maintain the mifepristone blood level above the necessary level. For example, if the mifepristone blood level is below 1631 ng/mL, the daily dose can be increased to 600 mg from 300 mg, to 900 mg from 600 mg, to 900 mg from 300 mg, to 1200 mg from 900 mg, to 1200 mg from 600 mg, or to 1200 mg from 300 mg. If after another seven daily doses, the mifepristone blood level is still not above the necessary level, the mifepristone daily can again be increased. For example, the mifepristone daily dose can be increased to 900 mg from 600 mg, to 1200 mg from 900 mg, or to 1200 mg from 600 mg. In some embodiments, the adjusting step comprises increasing the daily dose of the patient to achieve mifepristone blood levels greater than 1631 ng/mL. Additional adjustments in the daily doses can be made to maintain the mifepristone blood level above 1631 ng/mL.

Any suitable percentage of the patient population can have the optimal response to administration of the mifepristone. For example, at least 10, 20, 30, 40, 50, 60, 70, 80, 90 or 100% of the patient population can achieve the optimal response to the mifepristone treatment. In some embodiments, at least about 20% of the patient population can have the optimal response to administration of the mifepristone. In some embodiments, at least about 40% of the patient population can have the optimal response to administration of the mifepristone. In some embodiments, at least about 60% of the patient population can have the optimal response to administration of the mifepristone.

A. Patients in Need

Patients amenable to treatment with mifepristone according to the method of the present invention suffer from Cushing's syndrome. Cushing's syndrome is a disorder resulting from increased adrenocortical secretion of corticosteroid. Hyperfunction of the adrenal cortex may be adrenocorticotropic hormone (ACTH)-dependent or it may be independent of ACTH regulation, e.g. production of corticosteroid by an adrenocortical adenoma or carcinoma. A common cause of Cushing's syndrome is excessive production of ACTH by the pituitary gland. This elevated level of ACTH in the bloodstream typically is produced by a pituitary adenoma (Cushing's disease), but in rare instances has a different etiology. Cushing's syndrome resulting from the production of ACTH in a location other than the pituitary gland is known as ectopic Cushing's syndrome. Examples of ectopic sites include thymoma, medullary carcinoma of the thyroid, pheochromocytoma, islet cell tumors of the pancreas and oat cell carcinoma of the lung. The overwhelming majority of Cushing's syndrome cases in humans, however, trace their etiology to a pituitary adenoma. Symptoms of Cushing's syndrome include weight gain, central obesity, steroid hypersecretion, elevated urinary cortisol excretion, moon face, weakness, fatigue, backache, headache, impotence, mental status changes, muscle atrophy, and increased thirst and urination compared to mammals not suffering from this disease. Diagnosis and treatment of Cushing's syndrome remains a challenge (see Oldfield, E. W. et al., N. Engl. J. Med., 325:897-905 (1991); Findling, J. W. et al., "Diagnosis and differential diagnosis of Cushing's syndrome," Endocrinol. Metab. Clin. North Am., 30:729-47 (2001); Orth, D. N., "Cushing's syndrome," N Engl J. Med., 332:791-803 (1995)). In experienced specialized centers, surgical resection of ACTH-secreting pituitary microadenomas offers an overall cure rate of about 70-80%, but for macroadenomas cure rates only approximate 30%, and the extensive surgical resection required portends significant risk to surrounding normal pituitary tissue, leading to partial or total hypopituitarism in about 80% of cases (Simmons, N. E. et al., "Serum Cortisol response to transphenoidal surgery for Cushing disease," J. Neurosurg., 95:1-8 (2001); Mampalam, T. J. et al., "Transsphenoidal microsurgery for Cushing's disease: A report of 216 cases," Ann. Intern. Med., 109:487-93 (1988); and Trainer, P. J. et al., "Transsphenoidal resection in Cushing's disease: undetectable serum cortisol as the definition of successful treatment," Clin. Endocrinol., 38:73-8 (1993)).

B. Formulations of Mifepristone

Formulations of the present invention include mifepristone in combination with pharmaceutical excipients. Mifepristone is commercially available from a variety of sources such as Eurolabs Ltd. (London, England). Mifepristone can also be synthesized by one of skill in the art using known synthetic procedures.

Mifepristone refers to a family of compositions also referred to as RU486, or RU38.486, or 17-beta-hydroxy-11-beta-(4-dimethyl-aminophenyl)-17-alpha-(1-propynyl)-estra-4,9-dien-3-one), or 11-beta-(4dimethylaminophenyl)-17-beta-hydroxy-17-alpha-(1-propynyl)-estra-4,9-dien-3-one), or analogs thereof, which bind to the GR, typically with high affinity, and inhibit the biological effects initiated/mediated by the binding of any cortisol or cortisol analogue to a GR receptor. Chemical names for RU-486 vary; for example, RU486 has also been termed: 11B-[p-(Dimethylamino)phenyl]-17B-hydroxy-17-(1-propynyl)-estra-4,9-dien-3-one; 11B-(4-dimethyl-aminophenyl)-17B-hydroxy-17A-(prop-1-ynyl)-estra-4,9-dien-3-one; 17B-hydroxy-11B-(4-dimethylaminophenyl-1)-17A-(propynyl-1)-estra-4,9-diene-3-one; 17B-hydroxy-11B-(4-dimethylaminophenyl-1)-17A-(propynyl-1)-E; (11B,17B)-11-[4-dimethylamino)-phenyl]-17-hydroxy-17-(1-propynyl)estra-4,9-dien-3-one; and 11B-[4-(N,N-dimethylamino) phenyl]-17A-(prop-1-ynyl)-D-4,9-estradiene-17B-ol-3-one. Salts, hydrates and prodrug forms of mifepristone are also useful in the formulations of the present invention.

Formulations suitable for oral administration can consist of (a) liquid solutions, such as an effective amount of mifepristone suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form. The composition can, if desired, also contain other compatible therapeutic agents. Preferred pharmaceutical preparations can deliver the compounds of the invention in a sustained release formulation.

C. Administration of Mifepristone

The formulations of the present invention provide serum levels of mifepristone of at least 1631 ng/mL. The mifepristone utilized in the pharmaceutical method of the invention is administered at the initial dosage of about 0.001 mg/kg to about 1000 mg/kg daily. A daily dose range of about 0.01 mg/kg to about 500 mg/kg, or about 0.1 mg/kg to about 200 mg/kg, or about 1 mg/kg to about 100 mg/kg, or about 10 mg/kg to about 50 mg/kg, can be used. The dosages, however, may be varied depending upon the requirements of the patient and the condition being treated. The dose administered to a patient, in the context of the present invention, should be sufficient to effect a beneficial therapeutic response in the patient over time. The size of the dose also will be determined by the existence, nature, and extent of any adverse side-effects that accompany the administration of a particular compound in a particular patient. Determination of the proper dosage for a particular situation is within the skill of the practitioner.

Generally, treatment is initiated with six daily doses, with the blood levels tested on the day of the seventh daily dose in order to determine whether the dose used is providing a mifepristone blood level of at least 1631 ng/mL. The testing is also performed to ensure the blood levels are below those afforded by an LD50 dose of about 1000 mg/kg. If the mifepristone blood level is lower than 1631 ng/mL. Additional testing of mifepristone blood levels can be necessary in order to confirm a mifepristone blood level of at least 1631 ng/mL or to adjust the mifepristone daily dose higher. For convenience, the total daily dosage may be divided and administered in portions during the day, if desired. In addition, the interval from initiation of treatment and testing for mifepristone blood levels can be as short as 1 daily dose, or up to 28 daily doses and longer.

Mifepristone can be administered for any period of time, such as 7 daily doses over a period of seven days. Mifepristone can also be administered using more daily doses over a longer period of time, such as via 28 daily doses over a period of 28 days. Longer times for administration of mifepristone are also within the scope of the present invention.

D. Assay for Testing Mifepristone Levels

Mifepristone levels can be determined by any method known in the art. Methods for detecting mifepristone levels include, but are not limited to, radio-immuno assay and mass spectrometry (MALDI, SELDI, LS/MS, LS/MS/MS, among others). Liquid chromatography mass spectrometry (LC/MS or LC-MS) separates compounds chromatographically before they are introduced to the ion source and mass spectrometer. It differs from GC/MS in that the mobile phase is liquid, usually a combination of water and organic solvents, instead of gas. Most commonly, an electrospray ionization source is used in LC/MS.

Tandem mass spectrometry (MS/MS) involves multiple steps of mass selection or analysis, usually separated by some form of fragmentation. A tandem mass spectrometer is one capable of multiple rounds of mass spectrometry. For example, one mass analyzer can isolate one peptide from many entering a mass spectrometer. A second mass analyzer then stabilizes the peptide ions while they collide with a gas, causing them to fragment by collision-induced dissociation (CID). A third mass analyzer then catalogs the fragments produced from the peptides. Tandem MS can also be done in a single mass analyzer over time as in a quadrupole ion trap.

There are various methods for fragmenting molecules for tandem MS, including collision-induced dissociation (CID), electron capture dissociation (ECD), electron transfer dissociation (ETD), infrared multiphoton dissociation (IRMPD) and blackbody infrared radiative dissociation (BIRD). One of skill in the art will appreciate that other assays for testing mifepristone levels are known to one of skill in the art.

In some embodiments, the assay can be performed as follows. Blood is collected from a patient in a vacutainer containing sodium heparin. The blood is centrifuged and the resulting plasma frozen at an appropriate temperature until assay. In some embodiments, the temperature is about −70° C. In other embodiments, other blood components can be collected and stored. Prior to analysis, the plasma is thawed and a fraction of the plasma is mixed with an internal standard in a solvent such as acetonitrile, to obtain a fixed concentration of the standard. In some embodiments, the internal standard can be mifepristone-$d_4$. The concentration of the internal standard is selected in order to be greater than the expected concentration of mifepristone in the plasma. For example, the internal standard can have a concentration of 2000 ng/mL. One of skill in the art will appreciate that other internal standards, and other concentrations, are useful in the present invention.

Base is then added to the sample solution. The base can be any amine or ammonium base, such as ammonium hydroxide. One of skill in the art will appreciate that other bases are useful in the present invention.

Solvent is then added to the solution and the mifepristone (along with the internal standard) are extracted from the plasma. Solvents useful for the extraction of mifepristone include, but are not limited to, hexanes, pentanes, ethers (such as diethylether, tetrahydrofuran and methyl-t-butyl ether (MTBE)), ethyl acetate, chloroform and methylene chloride. One of skill in the art will appreciate that other solvents are useful in the present invention.

Following separation and concentration of the organic layer, the sample is reconstituted in a solvent mixture comprising water, acetonitrile and formic acid. The ratio of the solvent components can vary. In some embodiments, the solvent mixture is water:acetonitrile:formic acid (75:25:0.1, v/v/v). One of skill in the art will appreciate that other solvent mixtures are useful in the present invention.

The sample can then be analyzed by reverse-phase high pressure liquid chromatography (HPLC). In some embodiments, the reverse-phase HPLC is performed using a water:acetonitrile:formic acid (60:40:0.1) mobile phase (isocratic) at a flow rate of 0.3 mL/min. One of skill in the art will appreciate that other mobile phases and flow rates are useful in the present invention.

The reverse-phase HPLC column can be a phenyl column maintained at 50° C. Mifepristone elutes at 4.2 minutes. Following elution, the mobile phase can be nebulized using heated nitrogen in a Z-spray source/interface and the ionized compounds detected using a tandem quadrupole mass spectrometer. Mifepristone (molecular weight of 430 g/mol) can be detected at m/z 372.30. The internal standard mifepristone-$d_4$ can be detected at m/z 376.30. The ratio of the mifepristone peak height to the peak height for the internal standard can then be calculated.

The plasma concentration of mifepristone is then calculated by comparing the experimental ratio to a standard curve of mifepristone:mifepristone-$d_4$ peak height ratio v. mifepristone concentration. The standard curve is generated by first measuring the mifepristone:mifepristone-$d_4$ peak height ratios for mifepristone samples at 10, 20, 50, 100, 200, 500, 1000 and 2000 ng/mL where the mifepristone-$d_4$ internal standard has a concentration of 2000 ng/mL. The mifepristone:mifepristone-$d_4$ peak height ratios of these known solutions are then fit to a power equation (Mass Lynx by Micromass, Beverly, Mass.), against which future samples with unknown concentrations of mifepristone are compared.

The plasma levels of mifepristone derivatives such as RU42633, RU42698 and RU42848, among others, can also be determined using the assay described above.

E. Kits for Treating Cushing's Syndrome with Mifepristone

The present invention provides kits. The kits of the present invention comprise seven daily doses and a plasma sampling collection device. The kits of the present invention can also comprise any other component necessary for a kit, such as a container.

Patient plasma can be collected by any known plasma collection device. Some plasma collection devices useful in the present invention include, but are not limited to, vacutainers. The plasma collection devices of the present invention can optionally comprise additives in the device, such as anticoagulants (EDTA, sodium citrate, heparin, oxalate), a gel with intermediate density between blood cells and blood plasma, particles causing the blood to clot, a gel to separate blood cells from serum, thrombin and fluoride, among others.

The kits can also contain additional vessels used for further analysis of the plasma. For example, when the plasma is centrifuged, the centrifuged plasma can be transferred to a vessel, such as a cryostat tube. One of skill in the art will appreciate that other vessels and containers are useful in the present invention.

IV. Examples

Example 1: Determination of Mifepristone Plasma Level

This example provides a procedure for determining the plasma level of mifepristone in a patient.

Three (3) mL of blood was collected from a patient in a vacutainer containing sodium heparin. The blood was centrifuged and the resulting plasma frozen at −70 to −80° C. until assay. For analysis, the plasma samples were warmed and prepared as follows:

1. Using a pipette, 50.0 µL of the sample was aliquoted into a 16×100-mm glass test tube. When a partial volume aliquot was needed, the aliquot was added to the tube and diluted to full volume with blank human plasma.
2. 20.0 µL of the internal standard, mifepristone-$d_4$ (5.00 µg/mL in acetonitrile), was added to the tube, resulting in 2000.0 ng/mL mifepristone-$d_4$ in plasma.
3. The tube was vortexed for approximately 1 minute.
4. 50.0 µL of 6% ammonium hydroxide was added to the tube.
5. The tube was vortexed for approximately 1 minute.
6. 2.00 mL of MTBE was added to the tube.
7. 2.00 mL of hexane was added to the tube.
8. The tube was vortexed for at least 15 minutes.
9. The tube was centrifuged for at least 10 minutes at 2500 RPM (575×g).
10. The aqueous layer was frozen in a freezer set to maintain −70° C.
11. The upper organic layer was poured into a 13×100-mm polypropylene tube.
12. The organic layer was evaporated in a Turbovap set to 40° C.
13. 200.0 µL of a solution of water:acetonitrile:formic acid (75:25:0.1, v/v/v) was added to the tube.
14. The tube was vortexed for approximately 1 minute.
15. The tube was sonicated for approximately 1 minute.
16. The tube was vortexed for approximately 1 minute.
17. The sample was transferred to a labeled injection vial or well plate.
18. The vial or plate was capped and checked for air bubbles.

The sample was then analyzed by reverse-phase high pressure liquid chromatography using a water:acetonitrile:formic acid (60:40:0.1) mobile phase (isocratic) at a flow rate of 0.3 mL/min. The column was a phenyl column maintained at 50° C. Mifepristone elutes at 4.2 minutes. Following elution, the mobile phase was nebulized using heated nitrogen in a Z-spray source/interface and the ionized compounds detected using a tandem quadrupole mass spectrometer. Mifepristone (molecular weight of 430 g/mol) was detected at m/z 372.30. The internal standard mifepristone-$d_4$ was detected at m/z 376.30. The ratio of the mifepristone peak height to the mifepristone-$d_4$ peak height was calculated.

The plasma concentration of mifepristone was then calculated by comparing the experimental ratio to a standard curve of mifepristone:mifepristone-$d_4$ peak height ratio v. mifepristone concentration. The standard curve was generated by first measuring the mifepristone:mifepristone-$d_4$ peak height ratios for mifepristone samples at 10, 20, 50, 100, 200, 500, 1000 and 2000 ng/mL where the mifepristone-$d_4$ internal standard has a concentration of 2000 ng/mL. The mifepristone:mifepristone-$d_4$ peak height ratios of these known solutions were then fit to a power equation (Mass Lynx by Micromass, Beverly, Mass.), and the sample with unknown concentrations of mifepristone was compared.

Example 2: Treatment of Cushing's Syndrome

This example provides an open label study of the safety and efficacy in the treatment of Cushing's syndrome. The study was a Phase III trial performed using several investigators at several different sites. The objectives were to demonstrate the efficacy and safety of mifepristone in the treatment of Cushing's syndrome. The number of patients was 50. Patients eligible for randomization were male or nonpregnant female outpatients, and inpatients, if clinically required, with a diagnosis of Cushing's syndrome. Mifepristone was used as the test drug at 300 (1×300 mg tablet), 600 (2×300 mg tablet), 900 (3×300 mg tablet) and 1200 mg (4×300 mg tablet) once a day by mouth. Safety visits occurred at Days 21 and 35. If clinically necessary, a patient was treated as an inpatient. If early termination occurred prior to day 35, the patient returned for a safety follow up visit at day 35.

The primary efficacy endpoint was the proportion of patients with at least a 25% reduction from baseline on a standard two hour oral glucose tolerance test or a 5 month drop in their diastolic blood pressure at study end (6 months). The secondary endpoints were: (1) the patient's global impression; and (2) reduction in previously used antihypertensive medication.

Adverse events, laboratory assessments including electrocardiograms, and physical examination were used to assess safety.

The criteria for assessing study efficacy objective was the proportion of patients with at least a 25% reduction from baseline on a standard two hour oral glucose tolerance test or a 5 month drop in their diastolic blood pressure at study end (6 months).

TABLE 1

MIFE-C$_{trough}$ (ng/mL) at Each Dose Level Using the Subject Data Set for Responders who Completed the Study

| Parameter | MIFE-C$_{trough}$ (ng/mL) for Dose of: | | | |
|---|---|---|---|---|
| Dose | 300 | 600 | 900 | 1200 |
| N* | 30 | 29 | 23 | 14 |
| Mean | 1774.28 | 1951.66 | 2107.70 | 2292.86 |
| Median | 1455.00 | 1630.00 | 1820.00 | 2022.50 |
| Min | 820.00 | 890.00 | 992.00 | 1060.00 |
| Max | 4130.00 | 3850.00 | 4230.00 | 5440.00 |
| % CV | 46.1 | 43.2 | 44.1 | 47.3 |
| 95% CI Lower | 1469.15 | 1631.28 | 1706.19 | 1666.13 |
| 95% CI Upper | 2079.41 | 2272.04 | 2509.20 | 2919.58 |
| Optimal Response (%) | 20 | 20 | 20 | 40 |
| Cumulative Optimal Response (%) | 20 | 40 | 60 | 100 |

TABLE 2

Summary of MIFE-C$_{trough}$ Parameters and Prior Dose at First Response Including Early Terminators

| | MIFE-ΔC$_{trough}$ from Prior Dose (ng/mL) | MIFE-C$_{trough}$ at Response (ng/mL) |
|---|---|---|
| N | 26 | 31 |
| Mean | 221.50 | 1968.68 |
| SD | 582.96 | 834.99 |
| SE | 114.33 | 149.97 |
| Min | −860.00 | 448.00 |
| Median | 250.00 | 1770.00 |
| Max | 2017.00 | 4210.00 |
| % CV | 263.19 | 42.41 |
| 95% CI | 235.46 | 306.28 |
| Lower | −13.96 | 1662.40 |
| Upper | 456.96 | 2274.95 |

Example 3: Treatment of Male Patient with Cushing's Syndrome

A 50 year-old male, weighing 175 pounds, presents to physician with Cushing's syndrome. The physician prescribes 300 mg of mifepristone for seven daily doses over a period of seven days. One week later on the day of the seventh daily dose, three (3) mL of blood are collected from the patient and analyzed as described above in the specification. The dose of mifepristone is then adjusted, if necessary, to achieve mifepristone blood levels of greater than 1631 ng/mL. The mifepristone dose can be adjusted a single time to achieve mifepristone blood levels of greater than 1631 ng/mL. Alternatively, several adjustments to the mifepristone dose can be necessary to safely achieve mifepristone blood levels of greater than 1631 ng/mL.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A method of treating hypercortisolism in a patient, the method comprising:
   administering an initial daily dose of mifepristone once daily for at least seven days, wherein said initial daily dose is a dose selected from 300 milligrams (mg), 600 mg, and 900 mg of mifepristone;
   adjusting the dose amount of mifepristone to provide an adjusted daily dose of mifepristone if the plasma mifepristone level of the patient is less than 1631 ng/mL after administration of said at least seven days of administration of the initial daily dose of mifepristone, wherein said adjusted daily dose is a dose selected from 600 mg, 900 mg, and 1200 mg of mifepristone wherein said adjusting is performed in order to achieve a mifepristone plasma level of at least 1631 ng/mL; and
   administering to the patient said adjusted daily dose of mifepristone,
   thereby achieving a mifepristone plasma level of at least 1631 ng/mL
   with the proviso that the patient is not already suffering from a condition indicated for treatment with mifepristone,
   thereby treating hypercortisolism in the patient by achieving a mifepristone plasma level of at least 1631 ng/mL.

2. The method of claim 1, wherein administration of said doses of mifepristone comprises oral administration.

3. The method of claim 1, further comprising determining the mifepristone plasma level in a blood sample collected from the patient.

4. The method of claim 1, wherein the patient is treated with 28 or more daily doses over a period of 28 or more days.

5. The method of claim 4, wherein mifepristone plasma levels of at least 1631 ng/mL are achieved and maintained for up to six months.

6. The method of claim 1, wherein mifepristone plasma levels greater than 1631 ng/mL are achieved.

7. The method of claim 6, wherein the adjusting step comprises further adjusting the daily dose of the patient to maintain mifepristone plasma levels greater than 1631 ng/mL for up to six months.

8. The method of claim 1, wherein said patient treated for hypercortisolism is a patient suffering from Cushing's syndrome.

9. The method of claim 1, wherein said patient treated for hypercortisolism is a patient suffering from Cushing's disease.

10. The method of claim 1, wherein said patient treated for hypercortisolism is a patient suffering from adrenocorticotropin (ACTH)-dependent Cushing's syndrome.

11. The method of claim 1, wherein said patient treated for hypercortisolism is a patient suffering from adrenocorticotropin (ACTH)-independent Cushing's syndrome.

12. The method of claim 1, wherein said patient treated for hypercortisolism is a patient suffering from excess production of adrenocorticotropin (ACTH) by the pituitary gland.

13. The method of claim 12, wherein said patient treated for hypercortisolism is a patient suffering from a pituitary adenoma.

14. The method of claim 1, wherein said patient treated for hypercortisolism is a patient suffering from ectopic Cushing's syndrome.

15. The method of claim 14, wherein said ectopic Cushing's syndrome is caused by production of adrenocorticotropin (ACTH) in a location in which is found a thymoma, or a medullary carcinoma, or a pheochromocytoma, or an islet cell carcinoma of the pancreas, or an oat cell carcinoma.

* * * * *